United States Patent [19]

Davis

[11] Patent Number: 4,980,365

[45] Date of Patent: Dec. 25, 1990

[54] N-SUBSTITUTED-5,6-DIMETHOXY-1,2-BENZISOXAZOLE-3-PROPANAMINE AND RELATED COMPOUNDS AS ANALGESIC AND HYPOTENSIVE AGENTS

[75] Inventor: Larry Davis, Sergeantsville, N.J.

[73] Assignee: Hoechst-Roussel Pharmaceuticals Inc., Somerville, N.J.

[21] Appl. No.: 72,954

[22] Filed: Jul. 13, 1987

[51] Int. Cl.$^5$ .................. C07D 261/20; C07D 413/06; A61K 31/42; A61K 31/445

[52] U.S. Cl. ..................................... 514/379; 514/253; 514/321; 514/322; 544/368; 546/198; 546/199; 548/241

[58] Field of Search ........................ 514/379; 548/241

[56] References Cited

U.S. PATENT DOCUMENTS

| | | | |
|---|---|---|---|
| 4,374,245 | 2/1983 | Davis et al. | 546/20 |
| 4,390,544 | 6/1983 | Davis et al. | 546/198 |
| 4,396,770 | 8/1983 | Davis et al. | 546/198 |
| 4,458,075 | 7/1984 | Davis et al. | 546/198 |
| 4,536,578 | 8/1985 | Davis et al. | 544/360 |

FOREIGN PATENT DOCUMENTS

| | | | |
|---|---|---|---|
| 50368 | 5/1975 | Japan | 548/241 |
| 136666 | 11/1976 | Japan | . |

OTHER PUBLICATIONS

Pigini et al., *Eur. J. Med. Chem.* 10, p. 29 (1975).
Pigini et al., *Eur. J. Med. Chem.* 10, p. 33 (1975).
Uno et al., *Chem. Pharm. Bull.* 24, p. 632 (1976).
Pigini et al. I, Chemical Abstract No. 193144Y, (1975).
Pigini et al. II, Chemical Abstract No. 193145w (1975).
Uno et al. Chemical Abstract No. 39459c (1977).

*Primary Examiner*—Mukund J. Shah
*Assistant Examiner*—E. Bernhardt
*Attorney, Agent, or Firm*—Tatsuya Ikeda

[57] ABSTRACT

There are disclosed compounds having the formula

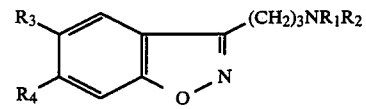

wherein $R_1$ is hydrogen or loweralkyl; $R_2$ is loweralkyl, arylloweralkyl, diarylloweralkyl or —CH$_2$CHOHCH$_2$OR$_5$, $R_5$ being aryl, or alternatively —NR$_1$R$_2$ taken together is

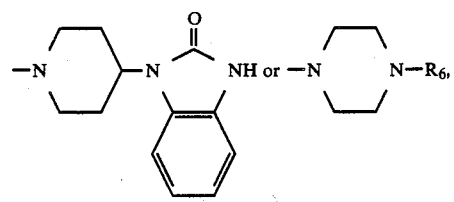

$R_6$ being aryl, arylloweralkyl, diarylloweralkyl,

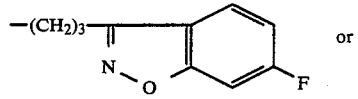

or

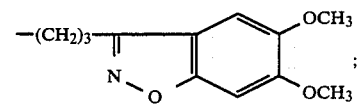

and $R_3$ and $R_4$ are each independently methoxy or hydroxy, which compounds are useful as analgesic and hypotensive agents.

20 Claims, No Drawings

N-SUBSTITUTED-5,6-DIMETHOXY-1,2-BENZISOXAZOLE-3-PROPANAMINE AND RELATED COMPOUNDS AS ANALGESIC AND HYPOTENSIVE AGENTS

This invention relates to compounds having formula I below

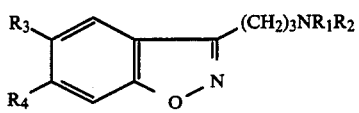

where $R_1$ is hydrogen or loweralkyl; $R_2$ is loweralkyl, arylloweralkyl, diarylloweralkyl or —$CH_2CHOHCH_2OR_5$, $R_5$ being aryl, or alternatively —$NR_1R_2$ taken together is

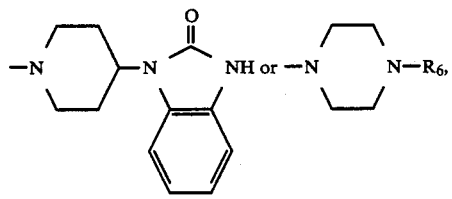

$R_6$ being aryl, arylloweralkyl, diarylloweralkyl,

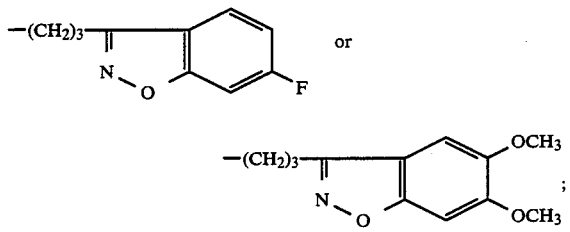

and $R_3$ and $R_4$ are each independently methoxy or hydroxy, which compounds are useful as analgesic and hypotensive agents; to pharmaceutical compositions comprising an effective amount of such a compound; to a method of alleviating pain which comprises administration of an effective amount of such a compound and to a method of reducing blood pressure which comprises administration of an effective amount of such a compound.

Throughout the specification and the appended claims, a given chemical formula or name shall encompass all stereo, optical and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated the term loweralkyl denotes a straight or branched alkyl group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently hydroxy, nitro, loweralkyl, loweralkoxy, halogen or $CF_3$.

The compounds of formula I are prepared by utilizing one or more of the reaction steps described below. Throughout the description of the synthetic steps, the definitions of $R_1$ through $R_6$ are as given above unless otherwise stated or indicated.

STEP A

The chloro compound of formula II is reacted with an amine of the formula III to obtain a compound of formula Ia.

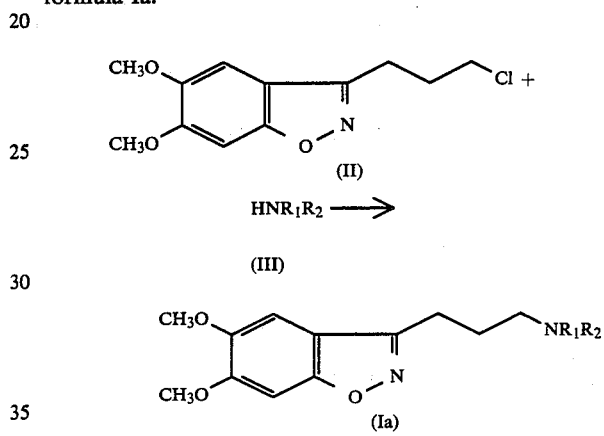

This reaction is typically conducted in the presence of milled $K_2CO_3$ (acid scavenger) and KI (catalyst) as well as a suitable solvent (including polar solvent) such as anhydrous dimethylformamide and stirring the reaction mixture at a temperature of about 50° to 100° C.

Where the group $R_1$ is loweralkyl in the above reaction step, the amine of formula III is prepared from the secondary amine $R_2$—$NH_2$ and loweralkyl chloride $R_1$—Cl in a routine manner known to the art.

STEP B

A compound of formula I where one or both of $R_3$ and $R_4$ are hydroxy is prepared by reacting compound Ia with pyridine hydrochloride in a routine manner known to the art.

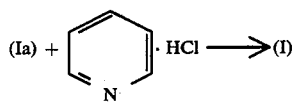

(where $R_3$ or $R_4$ or both are hydroxy)

STEP C

For introducing a substituent —$CH_2CHOHCH_2OR_5$ onto the amino nitrogen, the following scheme is used.

First, compound II is converted to the compound of formula IV in a routine manner known to the art (Gabriel synthesis).

(II) → 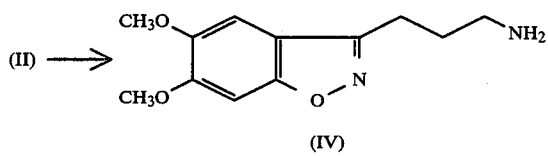
(IV)

Secondly, compound IV is reacted with an epoxy compound of formula V in a routine manner known to the art to afford a compound of formula VI.

(IV) + 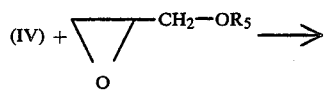 →

(V)

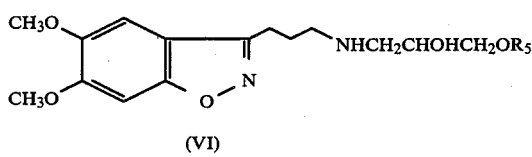
(VI)

Alternatively to the above, compound IV may be reacted with chloromethyloxirane in a routine manner known to the art to obtain the compound of formula VII and the latter reacted with an aryloxy anion of formula VIII in a routine manner known to the art to obtain compound VI.

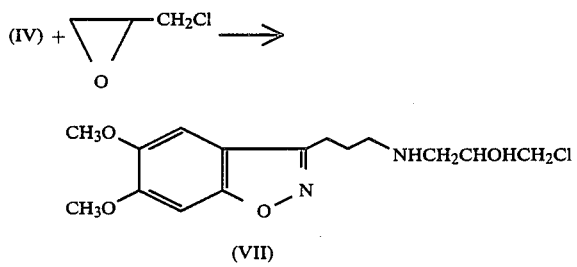
(VII)

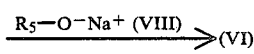 →(VI)

STEP D

The secondary amine hydrogen of compound VI can be replaced with a loweralkyl group $R_1$ in a routine manner known to the art to afford a compound of formula IX.

(VI) + $R_1$—Cl →

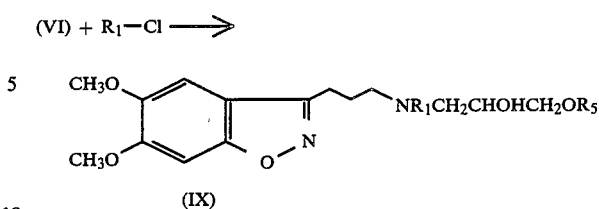
(IX)

STEP E

One or both of the methoxy groups in compound IX can be converted to hydroxy groups in substantially the same manner as described in STEP B.

(IX) + 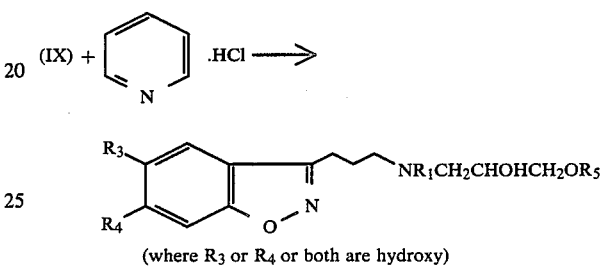

(where $R_3$ or $R_4$ or both are hydroxy)

(where $R_3$ or $R_4$ or both are hydroxy)

STEP F

Where the group —$NR_1R_2$ has the formula,

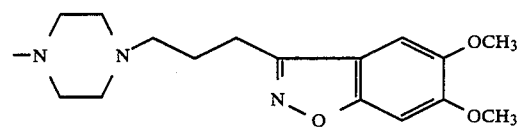

it is convenient to react piperazine with compound II at 1:2 stoichiometric ratio to obtain a compound formula X.

II + 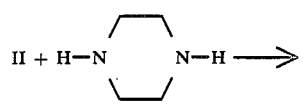 →

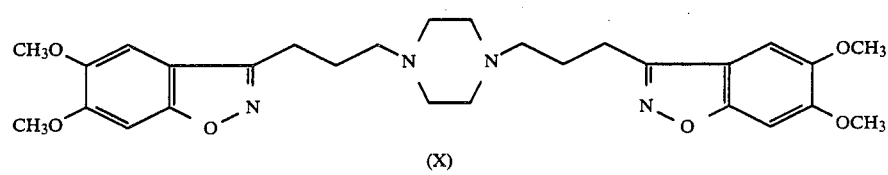
(X)

Compounds of this invention having formula I are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med. 15, 729 (1957)]. Table 1 shows test results for some of the compounds of this invention.

N-SUBSTITUTED-5,6-DIMETHOXY-1,2-BENZISOXAZOLE-3-PROPANAMINE AND RELATED COMPOUNDS AS ANALGESIC AND HYPOTENSIVE AGENTS

This invention relates to compounds having formula I below

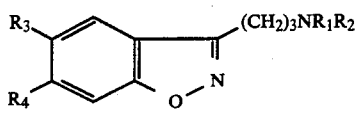 (I)

where $R_1$ is hydrogen or loweralkyl; $R_2$ is loweralkyl, arylloweralkyl, diarylloweralkyl or —CH$_2$CHOHCH$_2$OR$_5$, $R_5$ being aryl, or alternatively —NR$_1$R$_2$ taken together is

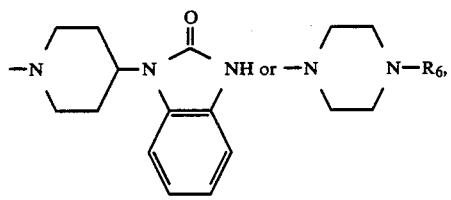

$R_6$ being aryl, arylloweralkyl, diarylloweralkyl,

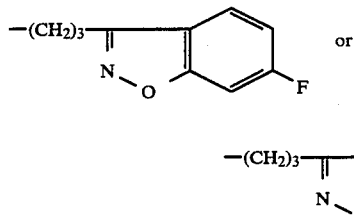

and $R_3$ and $R_4$ are each independently methoxy or hydroxy, which compounds are useful as analgesic and hypotensive agents; to pharmaceutical compositions comprising an effective amount of such a compound; to a method of alleviating pain which comprises administration of an effective amount of such a compound and to a method of reducing blood pressure which comprises administration of an effective amount of such a compound.

Throughout the specification and the appended claims, a given chemical formula or name shall encompass all stereo, optical and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated the term loweralkyl denotes a straight or branched alkyl group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently hydroxy, nitro, loweralkyl, loweralkoxy, halogen or CF$_3$.

The compounds of formula I are prepared by utilizing one or more of the reaction steps described below. Throughout the description of the synthetic steps, the definitions of $R_1$ through $R_6$ are as given above unless otherwise stated or indicated.

STEP A

The chloro compound of formula II is reacted with an amine of the formula III to obtain a compound of formula Ia.

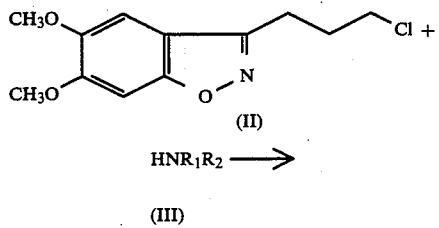

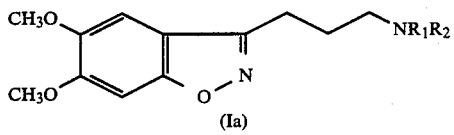

This reaction is typically conducted in the presence of milled K$_2$CO$_3$ (acid scavenger) and KI (catalyst) as well as a suitable solvent (including polar solvent) such as anhydrous dimethylformamide and stirring the reaction mixture at a temperature of about 50° to 100° C.

Where the group $R_1$ is loweralkyl in the above reaction step, the amine of formula III is prepared from the secondary amine $R_2$—NH$_2$ and loweralkyl chloride $R_1$—Cl in a routine manner known to the art.

STEP B

A compound of formula I where one or both of $R_3$ and $R_4$ are hydroxy is prepared by reacting compound Ia with pyridine hydrochloride in a routine manner known to the art.

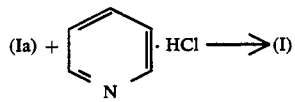

(where $R_3$ or $R_4$ or both are hydroxy)

STEP C

For introducing a substituent —CH$_2$CHOHCH$_2$OR$_5$ onto the amino nitrogen, the following scheme is used.

First, compound II is converted to the compound of formula IV in a routine manner known to the art (Gabriel synthesis).

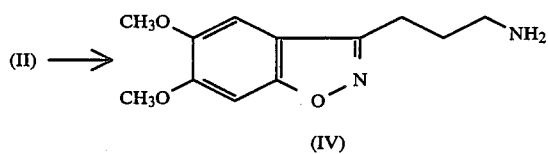

Secondly, compound IV is reacted with an epoxy compound of formula V in a routine manner known to the art to afford a compound of formula VI.

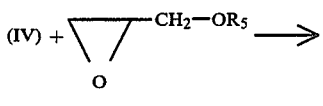

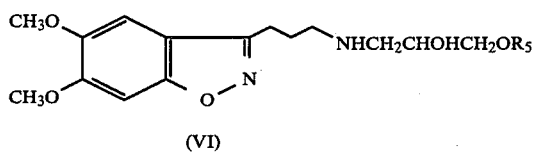

Alternatively to the above, compound IV may be reacted with chloromethyloxirane in a routine manner known to the art to obtain the compound of formula VII and the latter reacted with an aryloxy anion of formula VIII in a routine manner known to the art to obtain compound VI.

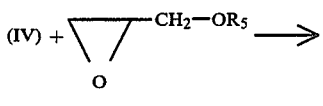

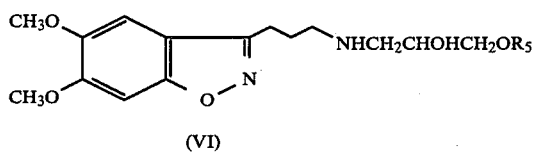

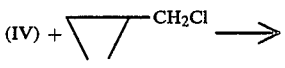

STEP D

The secondary amine hydrogen of compound VI can be replaced with a loweralkyl group $R_1$ in a routine manner known to the art to afford a compound of formula IX.

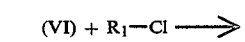

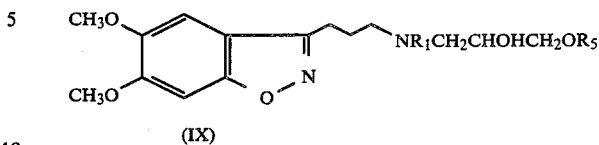

STEP E

One or both of the methoxy groups in compound IX can be converted to hydroxy groups in substantially the same manner as described in STEP B.

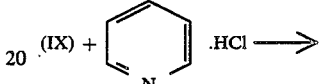

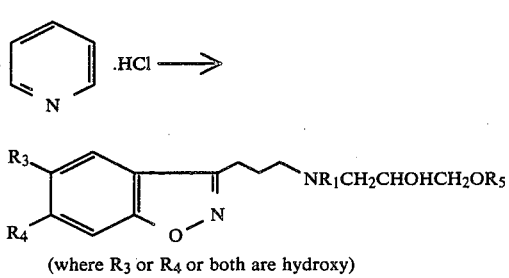

(where $R_3$ or $R_4$ or both are hydroxy)

(where $R_3$ or $R_4$ or both are hydroxy)

STEP F

Where the group $-NR_1R_2$ has the formula,

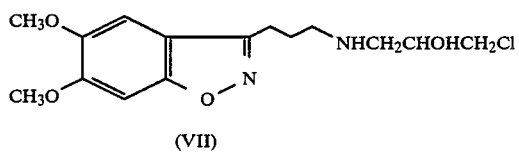

it is convenient to react piperazine with compound II at 1:2 stoichiometric ratio to obtain a compound formula X.

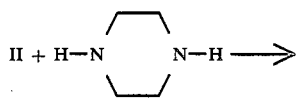

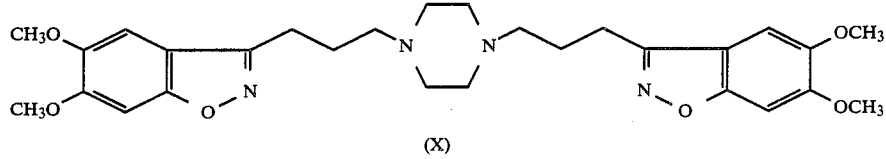

Compounds of this invention having formula I are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med. 15, 729 (1957)]. Table 1 shows test results for some of the compounds of this invention.

TABLE 1

Analgesic Activity
(Phenylquinone Writhing)

| Compound | ED$_{50}$ mg/kg, s.c. |
| --- | --- |
| N-methyl-N-(2-phenylethyl)-5,6-dimethoxy-1,2-benzisoxazole-3-propanamine | 13.6 |
| N-[2-(4-fluorophenyl)ethyl]-5,6-dimethoxy-1,2-benzisoxazole-3-propanamine | 3.8 |
| 3-[3-[4-(2-methoxyphenyl)-1-piperazinyl]-propyl]-5,6-dimethoxy-1,2-benzisoxazole | 1.7 |
| pentazocine (reference compound) | 1.3 |

Compounds of the present invention are also useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals are treated orally for three days with the test compound in relation to a control group of the same number. The drop in blood pressure is measured on the third day following administration. The antihypertensive activities of some of the compounds, expressed as a decrease in mean arterial blood pressure (in mm Hg), are given in Table 2.

TABLE 2

Antihypertensive Activity

| Compound | Pressure Drop (mmHg) at 50 mg/kg, p.o. |
| --- | --- |
| N-(2-phenylethyl)-5,6-dimethoxy-1,2-benzisoxazole-3-propanamine | 32 |
| 3-[3-[4-(2-methoxyphenyl)-1-piperazinyl]-propyl]-5,6-dimethoxy-1,2-benzisoxazole | 68 |
| Diltiazem (reference compound) | 39 |

Antihypertensive activities of the compounds of this invention can also be ascertained with reference to $\alpha_1$-adrenergic receptor antagonist activity as determined according to the method of Peroutka, et al., Neuropharmacology, 16, 549 (1977). The procedure used in this invention is described below.

[$^3$H]-WB4101: $\alpha_1$-ADRENERGIC RECEPTOR BINDING IN RAT BRAIN

This in vitro [$^3$H]-WB4101 receptor binding assay quantitates the primary blood pressure lowering effects through $\alpha_1$-receptor blockade. WB-4101 (2-(2,6-dimethoxyphenoxyethyl)aminoethyl-1,4-benzodioxane) is a specific and potent antagonist of the $\alpha_1$-adrenoceptor characterized in vitro in rat brain, heart, vascular smooth muscle and gastrointestinal smooth muscle. Peroutka et al. (1977) demonstrated a good correlation between the inhibition of $^3$H-WB4101 binding in brain membrane preparations and the blockade of peripheral vascular effects of norepinephrine. WB4101 labels an antagonist binding site on the $\alpha_1$-adrenoceptor, since it is preferentially displaced by antagonists while $\alpha$-noradrenergic agonists preferentially displace the $^3$H-agonists

PROCEDURE

This Assay method is adapted from the Peroutka article mentioned above.

Reagents 1. 0.5M Tris Buffer, pH 7.7 a. 57.2 g Tris HCl 16.2 g Tris base q.s. to 1 liter (0.5M Tris buffer, pH 7.7 at 25° C.).

b. Make a 1:10 dilution in distilled H$_2$O (0.05M Tris Buffer, pH 7.7)

2. [Phenoxy-3-$^3$H(N)]-WB4101, (2-(2,6-dimethoxyphenoxyethyl)aminomethyl-1,4-benzodioxane, (20–25 Ci/mmol) is obtained from New England Nuclear.

For IC$_{50}$ determination: $^3$H-WB4101 is made up to a concentration of 20 nM and 50 micro liter is added to each tube (yields a final concentration of 0.5 nM in the 2 ml assay volume).

3. L-norepinephrine bitartrate is obtained from Sigma Chemical Co.

A 10 mM stock solution of norepinephrine is made up in 0.01N HCl and 20 micro liter added to three tubes to determine nonspecific binding. This yields a final concentration of 100 micro liter in the assay.

4. Test Compounds

For most assays, a 1 mM stock solution is made up in a suitable solvent and serially diluted, such that the final concentration in the assay ranges from $10^{-5}$ to $10^{-8}$M. Seven concentrations are usually used for each assay. Higher or lower concentrations may be used, depending on the potency of the drug.

B. Tissue Preparation

Male Wistar rats (100–150 g) are killed by decapitation and their brains rapidly removed. Whole brains minus cerebella are homogenized in 50 volumes of ice-cooled 50 mM Tris buffer (pH 7.7 at 25° C.) using a Tekmar homogenizer. The homogenate is centrifuged at 40,000 g, the supernatant discarded and the pellet resuspended in fresh 50 mM Tris buffer and recentrifuged at 40,000 g. The final pellet is resuspended in the original volume of fresh 50 mM Tris buffer, pH 7.7. The final tissue concentration in the assay is 10 mg/ml. Specific binding is approximately 9% of the total added ligand and approximately 80% of the total bound ligand.

C. Assay

| | |
| --- | --- |
| 100 micro liter | 0.05M Tris buffer, pH 7.7 |
| 830 micro liter | H$_2$O |
| 20 micro liter | Vehicle (for total binding) or 10 mM L-NE (for nonspecific binding) or appropriate drug concentrations |
| 50 micro liter | $^3$H-WB4101 stock solution |
| 1000 micro liter | Tissue suspension |

Sample tubes are kept on ice for additions, then vortexed and incubated for 15 minutes at 15° C. The binding is terminated by rapid vacuum filtration through Whatman GF/B filters, followed by three 5 ml washes with ice-cold 0.05M Tris buffer. The filters are counted in 10 ml of liquid scintillation cocktail. Specific WB 4101 binding is defined as the difference between the total binding and that bound in the presence of 100 micro molar NE. IC$_{50}$ calculations are performed using computer derived log-probit analysis.

Test results for some of the compounds of this invention are presented in Table 3.

TABLE 3

$\alpha_1$-adrenergic receptor antagonist activity (IC$_{50}$)

| Compound | [$^3$H]-WB4101: $\alpha_1$-Adrenergic Receptor (IC$_{50}$) Antagonist Activity |
| --- | --- |
| N-(2-phenylethyl)-5,6-dimethoxy- | 8.3 × 10$^{-8}$M |

TABLE 3-continued

| Compound | $\alpha_1$-adrenergic receptor antagonist activity ($IC_{50}$) [$^3$H]-WB4101: $\alpha_1$-Adrenergic Receptor ($IC_{50}$) Antagonist Activity |
|---|---|
| 1,2-benzisoxazole-3-propanamine N-methyl-N-(2-phenylethyl)-5,6-dimethoxy-1,2-benzisoxazole-3-propanamine | $6.7 \times 10^{-8}$M |
| phenoxybenzamine (reference compound) | $1.2 \times 10^{-8}$M |
| Prazocin (reference compound) | $8.0 \times 10^{-10}$M |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposable syringes or multiple dose vials made of glass or plastic.

Examples of the compounds of this invention include:
N-(phenylmethyl)-5,6-dimethoxy-1,2-benzisoxazole-3-propanamine;
N-[(2,4-dimethoxy)phenylmethyl]-5,6-dimethoxy-1,2-benzisoxazole-3-propanamine;
N-methyl-N-(phenylmethyl)-5,6-dimethoxy-1,2-benzisoxazole-3-propanamine;
N-(2-phenylethyl)-5,6-dimethoxy-1,2-benzisoxazole-3-propanamine;
N-[2-(4-fluorophenyl)ethyl]-5,6-dimethoxy-1,2-benzisoxazole-3-propanamine;
N-[2-(4-nitrophenyl)ethyl]-5,6-dimethoxy-1,2-benzisoxazole-3-propanamine;
N-[2-(3,4-dimethoxyphenyl)ethyl]-5,6-dimethoxy-1,2-benzisoxazole-3-propanamine;
N-methyl-N-(2-phenylethyl)-5,6-dimethoxy-1,2-benzisoxazole-3-propanamine;
N-[2-(3,4-dimethoxyphenyl)ethyl]-N-methyl-5,6-dimethoxy-1,2-benzisoxazole-3-propanamine;
N-[2-(3,4-dimethoxyphenyl)ethyl]-N-methyl-6-hydroxy-5-methoxy-1,2-benzisoxazole-3-propanamine;
N-[3-(diphenyl)propyl]-N-methyl-5,6-dimethoxy-1,2-benzisoxazole-3-propanamine;
N-[(2-hydroxy-3-phenoxy)propyl]-5,6-dimethoxy-1,2-benzisoxazole-3-propanamine;
3-[3-[4-[2-oxobenzimidazol-1-yl]-1-piperidinyl]propyl]-5,6-dimethoxy-1,2-benzisoxazole;
3-[3-[4-(2-methoxyphenyl)-1-piperazinyl]propyl]-5,6-dimethoxy-1,2-benzisoxazole;
3-[3-(4-diphenylmethyl-1-piperazinyl)propyl]-5,6-dimethoxy-1,2-benzisoxazole;
3-[3-[4-(2,3,4-trimethoxyphenyl)-1-piperazinyl]propyl]-5,6-dimethoxy-1,2-benzisoxazole;
3-[3-[4-[bis(4-fluorophenyl)methyl]-1-piperazinyl]propyl]-5,6-dimethoxy-1,2-benzisoxazole;
3-[3-[4-[(4-chlorophenyl)phenylmethyl]-1-piperazinyl]propy]-5,6-dimethoxy-1,2-benzisoxazole;
3-[3-[4-[4-[bis(4-fluorophenyl)butyl]]-1-piperazinyl]propyl]-5,6-dimethoxy-1,2-benzisoxazole;
3-[3-[4-[3-[6-fluoro-1,2-benzisoxazol-3-yl]propyl]-1-piperazinyl]propyl]-5,6-dimethoxy-1,2-benzisoxazole; and 3-[3-[4-[3-[5,6-dimethoxy-1,2-benzisoxazol-3-yl]propyl]-1-piperazinyl]propyl]-5,6-dimethoxy-1,2-benzisoxazole.

The following examples are presented in order to illustrate this invention.

EXAMPLE 1

N-(phenylmethyl)-5,6-dimethoxy-1,2-benzisoxazole-3-propanamine hydrochloride

To 75 ml of dry dimethylformamide (DMF) were added 3-(3-chloropropyl)-5,6-dimethoxy-1,2-benzisoxazole (5.0 g), benzylamine (4.5 ml), milled potassium carbonate (10 g) and potassium iodide (0.01 g).

After five hours of stirring at 80° C., the mixture was poured into 500 ml of water, stirred for five minutes and then extracted with ethyl acetate. The organic layer was washed with water (2X) and thereafter dried (saturated sodium chloride, anhydrous magnesium sulfate).

After filtration, the solvent was evaporated, leaving about 10 g of oil which was eluted on a silica gel column with 5% methanol/dichloromethane (DCM) via high performance liquid chromatography (HPLC). The desired fractions were combined and concentrated to about 4 g of oil.

This oil was dissolved in ether, the pH adjusted to 1 with etheral-HCl, and the resultant precipitate collected and dried, 3.2 g, d @240° C. This material was recrystallized from isopropanol/ether (1:10) to yield 2.3 g of crystals, d @240° C.

| ANALYSIS | | | |
|---|---|---|---|
| Calculated for $C_{19}H_{22}N_2O$.HCl: | 62.89% C | 6.39% H | 7.72% N |
| Found: | 62.75% C | 6.36% H | 7.63% N |

EXAMPLE 2

N-[(2,4-dimethoxy)phenylmethyl]-5,6-dimethoxy-1,2-benzisoxazole-3-propanamine hydrochloride To 90 ml of dry DMF were added 3-(3-chloropropyl)-5,6-dimethoxy-1,2-benzisoxazole (5.1 g), 2,4-dimethoxybenzylamine hydrochloride (8.1 g), milled potassium carbonate (20 g) and potassium iodide (0.01 g).

After six hours of stirring at 90° C., the mixture was poured into 500 ml of water, stirred for five minutes and then extracted with ethyl acetate/ether. The organic layer was washed with water (2×100 ml) and saturated sodium chloride solution (1×100 ml), and then dried over anhydrous magnesium sulfate.

After filtration, the solvents were evaporated, leaving about 10 g of oil which was eluted on a silica gel column with 5% methanol/DCM via HPLC. The desired fractions were combined, concentrated to 4 g of oil, dissolved in ether and then acifidied to pH 1 with ethereal-HCl. The resultant precipitate was collected and dried to yield 3.0 g, d @210° C. This material was recrystallized from methanol/ether (1:5) to yield 2.5 g of solid, d @214° C.

| ANALYSIS | | | |
|---|---|---|---|
| Calculated for $C_{21}H_{26}N_2O_5$.HCl: | 59.46% C | 6.44% H | 6.63% N |
| Found: | 59.53% C | 6.37% H | 6.54% N |

EXAMPLE 3

N-methyl-N-(phenylmethyl)-5,6-dimethoxy-1,2-benzisoxazole-3-propanamine oxalate

To 75 ml of dry DMF were added 3-(3-chloropropyl)-5,6-dimethoxy-1,2-benzisoxazole (5.1 g), N-benzylmethylamine (2.4 ml), milled $K_2CO_3$ (10 g) and KI (0.01 g).

After seven hours of stirring at 90° C., the mixture was poured into 200 ml of water, stirred for five minutes and then extracted with ether/ethyl acetate. The organic layer was washed with water (2X) and saturated NaCl, and then dried over anhydrous magnesium sulfate.

After filtration, the solvents were evaporated, leaving about 10 g of oil, which was eluted on a silica gel column with 5% methanol/DCM via HPLC. The desired fraction was collected, concentrated to about 5 g of oil, dissolved in ether, and then acidified to pH 1 with ethereal oxalic acid.

The resultant precipitate was collected and dried to yield 2.6 g of solid, d @110° C. This material was recrystallized from isopropanol to yield 2.3 g of crystals, d @132° C.

| ANALYSIS | | | |
|---|---|---|---|
| Calculated for $C_{20}H_{24}N_2O_3.C_2H_2O_4$: | 61.38% C | 6.09% H | 6.51% N |
| Found: | 61.49% C | 6.18% H | 6.47% N |

EXAMPLE 4

N-(2-phenylethyl)-5,6-dimethoxy-1,2-benzisoxazole-3-propanamine hydrochloride

To 100 ml of dry DMF were added 3-(3-chloropropyl)-5,6-dimethoxy- 1,2-benzisoxazole (6.4 g), 2-(phenyl)ethylamine (6.05 g), milled $K_2CO_3$ g) and KI (0.01 g)

After six hours of stirring at 90° C., the mixture was poured into 500 ml of water, stirred for five minutes and then extracted with ether/ethyl acetate. The organic layer was washed with water (2×100 ml) and saturated NaCl (1×100 ml), and then dried over anhydrous $MgSO_4$.

After filtration, the solvents were evaporated, leaving about 12 g of oil which was eluted on a silica gel column with 5% methanol/DCM via HPLC. The desired fractions were combined and concentrated to 4.3 g of oil.

This oil was dissolved in ether, the pH of the solution adjusted to 1 with ethereal-HCl, and the resultant precipitate collected and dried to yield 3.4 g, d @220° C. This material was recrystallized from methanol/ether (1:1) to yield 3.0 g of crystals, d @227° C.

| ANALYSIS | | | |
|---|---|---|---|
| Calculated for $C_{20}H_{24}N_2O_3$.HCl: | 63.73% C | 6.69% H | 7.43% N |
| Found: | 63.55% C | 6.70% H | 7.34% N |

EXAMPLE 5

N-[2-(4-fluorophenyl)ethyl]-5,6-dimethoxy-1,2-benzisoxazole-3-propanamine hydrochloride To 100 ml of dry DMF were added 2-(4-fluorophenyl)ethylamine hydrochloride (10 g) and milled $K_2CO_3$ (20 g). After five minutes of stirring, 3-(3- chloropropyl)-5,6-dimethoxy-1,2-benzisoxazole (6.4 g) and KI (0.01 g) were added.

After fourteen hours of stirring at 90° C., the mixture was filtered and the filtrate was concentrated to a dark oil, stirred with water and then extracted with ether. The ether solution was washed with water (2X) and then dried (saturated NaCl, anhydrous MgSO$_4$).

After filtration, the solvent was evaporated, leaving about 11 g of oil, which was eluted on a silica gel column with 5% methanol/DCM. The desired fractions were combined and concentrated to 3.8 g of oil which was dissolved in ether, the pH was adjusted to 1 with etheral-HCl, and the resultant precipitate collected and dried to give 3.5 g, d @210° C. This material was recrystallized twice from methanol/ether (1:2) to give 2.3 g of crystals, d @228° C.

| ANALYSIS | | | |
|---|---|---|---|
| Calculated for $C_{20}H_{23}FN_2O_3$·HCl: | 60.83% C | 6.13% H | 7.10% N |
| Found: | 60.79% C | 6.44% H | 7.00% N |

EXAMPLE 6

N-[2-(4-nitrophenyl)ethyl]-5,6-dimethoxy-1,2-benzisoxazole-3-propanamine hydrochloride To 100 ml of dry DMF were added 3-(3-chloropropyl)-5,6-dimethoxy-1,2-benzisoxazole (6.4 g), (4-nitrophenyl)ethylamine hydrochloride (10 g), milled K$_2$CO$_3$ (20 g) and KI (0.01 g).

After twelve hours of stirring at 90° C., the mixture was poured into 500 ml of water and then extracted with ethyl acetate. The organic layer was washed with water (2X) and then dried (saturated NaCl, anhydrous MgSO$_4$).

After filtration, the solvent was evaporated, leaving about 16 g of oil, which was eluted on a silica gel column with 4% methanol/DCM via HPLC. The desired fractions were combined and concentrated to 3.0 g of oil, which solidified on standing, m.p. 96° C.

This material was dissolved in ether, pH adjusted to 1 with etheral-HCl, and the resultant precipitate collected and dried to yield 2.5 g, d @175° C. This was recrystallized from methanol/ether (1:2) to give 2.0 g of solid, d @188° C.

| ANALYSIS | | | |
|---|---|---|---|
| Calculated for $C_{20}H_{23}N_3O_5$·HCl: | 56.94% C | 5.73% H | 9.96% N |
| Found: | 56.90% C | 5.61% H | 10.01% N |

EXAMPLE 7

N-[2-(3,4-dimethoxyphenyl)ethyl]-5,6-dimethoxy-1,2-benzisoxazole-3-propanamine oxalate To 100 ml of dry DMF were added 3-(3-chloropropyl)-5,6-dimethoxy-1,2-benzisoxazole (5.1 g), 2-(3,4-dimethoxyphenyl)ethylamine (7.2 g), milled K$_2$CO$_3$ (20 g) and KI (0.01 g).

After six hours of stirring at 80° C., the mixture was poured into 500 ml of water, stirred for five minutes and then extracted with ethyl acetate/ether. The organic layer was washed with water (2×100 ml) and saturated NaCl (1×100 ml), and then dried over anhydrous MgSO$_4$.

After filtration, the solvents were evaporated, leaving 8 g of oil which was eluted on a silica gel column with 8% methanol/DCM via HPLC. The desired fractions were combined and concentrated to 3 g of oil, which was dissolved in ether/ethyl acetete and acidified to pH 1 with ethereal oxalic acid. The resultant precipitate was collected and dried to yield 3.0 g, d @192° C. This material was recrystallized from methanol to yield 2.8 g, d @196°–7° C.

| ANALYSIS | | | |
|---|---|---|---|
| Calculated for $C_{22}H_{28}N_2O_5$·$C_2H_2O_4$: | 58.76% C | 6.17% H | 5.71% N |
| Found: | 58.77% C | 6.18% H | 5.63% N |

EXAMPLE 8

N-methyl-N-(2-phenylethyl)-5,6-dimethoxy-1,2-benzisoxazole-3-propanamine oxalate To 75 ml of DMF were added 3-(3-chloropropyl)-5,6-dimethoxy-1,2-benzisoxazole (4.0 g), N-methylphenylethylamine (2.0 g), milled K$_2$CO$_3$ (5.0 g) and KI (0.01 g).

After six hours of stirring at 90° C. and twenty hours at ambient temperature, the mixture was poured into 300 ml of water, stirred for five minutes, and then extracted with ethyl acetate/ether. The organic layer was washed with water (2X), and then dried (saturated NaCl, anhydrous MgSO$_4$).

After filtration, the solvents were evaporated, leaving about 5 g of oil, which was eluted on a silica gel column with ethyl acetate via HPLC. The desired fraction was collected and concentrated to 2.6 g of oil. This oil was dissolved in ether and acidified to pH 1 with ethereal-oxalic acid. The resultant precipitate was collected and dried to yield 2.8 g, d @157° C. This material was recrystallized from isopropanol/ether (1:10) to yield 2.2 g of solid, d @157° C.

| ANALYSIS | | | |
|---|---|---|---|
| Calculated for $C_{21}H_{26}N_2O_3$·(CO$_2$H)$_2$: | 62.15% C | 6.35% H | 6.30% N |
| Found: | 62.40% C | 6.40% H | 6.32% N |

EXAMPLE 9

N-[2-(3,4-dimethoxyphenyl)ethyl]-N-methyl-5,6-dimethoxy-1,2-benzisoxazole-3-propanamine oxalate To 50 ml of DMF were added 3-(3-chloro-5,6-dimethoxy-1,2-benzisoxazole (5.0 g), N-[2-(3,4-dimethoxyphenethyl)]-N-methylamine (3.4 g), milled K$_2$CO$_3$ (4.0 g) and KI (0.01 g).

After five hours of stirring at 80° C., the mixture was poured into 500 ml of water, stirred for five minutes and then extracted with ethyl acetate. The organic layer was collected, washed with water (2X) and dried (saturated NaCl, anhydrous MgSO$_4$).

After filtration, the solvent was evaporated, leaving 8 g of oil, which was purified via HPLC on silica gel using 3% methanol/DCM as the eluting solvent. The desired fraction was collected and concentrated to 5 g of oil. This oil was dissolved in ether, the pH adjusted to 1 with ethereal-oxalic acid, and the resultant precipitate collected and dried to yield 4.0 g, d @146° C. This material was recrystallized from dichloromethane/ether (1:1) to yield crystals, d @146° C.

| ANALYSIS | | | |
|---|---|---|---|
| Calculated for $C_{23}H_{30}N_2O_5 \cdot (CO_2H)_2$: | 59.51% C | 6.39% H | 5.55% N |
| Found: | 59.33% C | 6.28% H | 5.55% N |

EXAMPLE 10

N-[2-(3,4-dimethoxyphenyl)ethyl]-N-methyl-6-hydroxy-5-methoxy-1,2-benzisoxazole-3-propanamine To 70 ml of dry DMF were added 3-(3-chloropropyl)-6-hydroxy-5-methoxy-1,2-benzisoxazole (4.4 g), N-[2-(3,4-dimethoxyphenethyl)]-methylamine (3.0 g), $NaHCO_3$ (10 g) and KI (0.01 g).

After four hours of stirring at 90° C., the mixture was poured into 200 ml of water, stirred for five minutes and then extracted with ethyl acetate. The ethyl acetate layer was washed with water (2×100 ml) and saturated NaCl (1×100 ml), and then dried over anhydrous $MgSO_4$.

After filtration, the solvent was evaporated, leaving about 8 g of oil, which was eluted on a silica gel column with 10% methanol/DCM via HPLC. The desired fraction was concentrated to a brown oil, which solidified to 4 g of solid, m.p. 98°–100° C. This material was recrystallized twice from isopropyl ether/methanol (10:1) to yield 2.5 g of solid, m.p. 112°–3° C.

| ANALYSIS | | | |
|---|---|---|---|
| Calculated for $C_{22}H_{28}N_2O_5$: | 65.98% C | 7.05% H | 7.00% N |
| Found: | 65.56% C | 7.06% H | 6.86% N |

EXAMPLE 11

N-[3-(diphenyl)propyl]-N-methyl-5,6-dimethoxy-1,2-benzisoxazole-3-propanamine oxalate To 100 ml of dry DMF were added 3-(3-chloropropyl)-5,6-dimethoxy-1,2-benzisoxazole (6.0 g), N-methyl-3,3-diphenylpropylamine (5.6 g), milled $K_2CO_3$ (10 g), and KI (0.01 g).

After seven hours of stirring at 90° C., the mixture was poured into 500 ml of water, stirred for five minutes and then extracted with ether/ethyl acetate. The organic layer was washed with water (2X) and dried (saturated NaCl, anhydrous $MgSO_4$).

After filtration, the solvents were evaporated, leaving about 11 g of oil, which was eluted on a silica gel column with ethyl acetate via HPLC. The desired fraction was concentrated to about 4 g of oil, which was dissolved in ether, and acifidied to pH 1 with ethereal-oxalic acid. The resultant precipitate was collected, washed with ether, and then dried to yield 3.8 g, d @65° C. This material was recrystallized from isopropanol/ether (1:5) to give 3.0 g of crystals, d @137° C.

| ANALYSIS | | | |
|---|---|---|---|
| Calculated for $C_{28}H_{32}N_2O_3 \cdot C_2H_2O_4$: | 65.86% C | 6.71% H | 5.49% N |
| Found: | 65.97% C | 6.59% H | 5.02% N |

EXAMPLE 12

N-[(2-hydroxy-3-phenoxy)propyl]-5,6-dimethoxy-1,2-benzisoxazole-3-propanamine oxalate To 75 ml of dry DMF were added 3-(3-chloropropyl)-5,6-dimethoxy-1,2-benzisoxazole (3.8 g), 2-hydroxy-3-phenoxypropylamine (5.0 g), milled $K_2CO_3$ (10 g) and KI (0.01 g).

After seven hours of stirring at 90° C., the mixture was poured into 200 ml of water, stirred for five minutes and then extracted with ethyl acetate. The organic layer was washed with water (2X) and saturated NaCl, and then dried over anhydrous $MgSO_4$.

After filtration, the solvent was evaporated, leaving about 7 g of oil, which was eluted on a silica gel column with 8% methanol/DCM via HPLC. The desired fractions were combined and concentrated to about 3 g of oil, which was dissolved in ether and then acidified to pH 1 with ethereal-oxalic acid. The resultant precipitate was collected and dried to yield 3.0 g (d @135° C.). This material was recrystallized twice from isopropanol/methanol (1:1) to yield 2.3 g of solid, d @180° C.

| ANALYSIS | | | |
|---|---|---|---|
| Calculated for $C_{21}H_{26}N_2O_5 \cdot C_2H_2O_4$: | 57.97% C | 5.92% H | 5.88% N |
| Found: | 58.53% C | 5.93% H | 6.00% N |

EXAMPLE 13

3-[3-[4-[2-oxobenzimidazol-3-yl]-1-piperidnyl]propyl]-5,6-dimethoxy-1,2-benzisoxazole hydrochloride To 80 ml of dry DMF were added 3-(3-chloropropyl)-5,6-dimethoxy-1,2-benzisoxazole (5.0 g), 4-(2-oxo-1-benzimidazol-1-yl)piperidine (4.3 g), milled $K_2CO_3$ (10 g) and KI (0.01 g).

After four hours of stirring at 85° C., the mixture was poured into 200 ml of water, stirred for five minutes and then extracted with ethyl acetate. The organic layer was washed with water (2X) and dried (saturated NaCl, anhydrous $MgSO_4$).

After filtration, the solvents were evaporated, leaving 10 g of solid which was eluted on a silica gel column with 5% methanol/DCM via HPLC. The desired fractions were combined and concentrated to 5 g of solid, which was dissolved in warm isopropanol and acidified to pH 1 with etheral-HCl. The mixture was cooled and diluted with ether, whereupon a solid precipitated, which was collected and dried to give 6.0 g, m.p. ~255° C.

| ANALYSIS | | | |
|---|---|---|---|
| Calculated for $C_{24}H_{28}N_4O_4 \cdot HCl$: | 60.94% C | 6.18% H | 11.85% N |
| Found: | 60.61% C | 6.21% H | 11.74% N |

EXAMPLE 14

3-[3-[4-(2-methoxyphenyl)-1-piperazinyl]propyl]-5,6-dimethoxy-1,2-benzisoxazole

To 80 ml of dry DMF were added 3-(3-chloropropyl)-5,6-dimethoxy-1,2-benzisoxazole (6.4 g), 4-(2-methoxyphenyl)piperazine (3.8 g), milled $K_2CO_3$ (10 g) and KI (0.1 g).

After three hours of stirring at 85° C., the mixture was poured into 200 ml of water and extracted with ethyl acetate. The organic layer was washed with water (2X) and dried (saturated NaCl, anhydrous $MgSO_4$).

After filtration, the solvent was evaporated, leaving about 8 g of oil, which was eluted on a silica gel column with 3% methanol/DCM via HPLC. The desired fractions were combined and concentrated to an oil, which was dissolved in ether, the pH adjusted to 1 with ethereal-HCl, and the resultant precipitate collected and dried to give 2.7 g, d @220° C.

| ANALYSIS | | | |
|---|---|---|---|
| Calculated for $C_{23}H_{29}N_3O_4$.HCl: | 61.67% C | 6.75% H | 9.38% N |
| Found: | 61.49% C | 6.61% H | 9.24% N |

EXAMPLE 15

3-[3-(4-diphenylmethyl-1-piperazinyl)propyl]-5,6-dimethoxy-1,2-benzisoxazole oxalate To 75 ml of dry DMF were added 3-(3-chloropropyl)-5,6-dimethoxy-1,2-benzisoxazole (3.5 g), 1-(diphenylmethyl)piperazine (3.5 g), milled $K_2CO_3$ (10 g) and KI (0.01 g).

After six hours of stirring at 90° C., the mixture was poured into 500 ml water, stirred for five minutes and then extracted with ethyl acetate. The ethyl acetate layer was washed with water (2X) and dried (saturated NaCl, anhydrous $MgSO_4$).

After filtration, the solvent was evaporated, leaving about 7 g of oil which was eluted on a silica gel column with ethyl acetate via HPLC. The desired fraction was concentrated to about 4 g of oil which was dissolved in ethyl ether and the pH adjusted to 1 with ethereal oxalic acid. The resultant precipitate was collected and dried to yield 4.0 g, d @115° C. This material was recrystallized twice from isopropanol/methanol (1:1) to yield 2.7 g, d @228° C.

| ANALYSIS | | | |
|---|---|---|---|
| Calculated for $C_{29}H_{33}N_3O_3.C_2H_2O_4$ | 66.29% C | 6.28% H | 7.48% N |
| Found: | 66.13% C | 6.43% H | 7.40% N |

EXAMPLE 16

3-[3-[4-(2,3,4-trimethoxyphenyl)-1-piperazinyl]propyl]-5,6-dimethoxy-1,2-benzisoxazole oxalate To 75 ml of dry DMF were added 3-(3-chloropropyl)-5,6-dimethoxy-1,2-benzisoxazole (3.5 g), N-(2,3,4-trimethoxybenzyl)piperazine (3.5 g), milled $K_2CO_3$ (10 g) and KI (0.01 g).

After seven hours of stirring at 90° C., the mixture was poured into 300 ml of water, stirred for five minutes and then extracted with ethyl acetate. The ethyl acetate layer was washed with water (2X) and dried (saturated NaCl, anhydrous $MgSO_4$).

After filtration, the solvent was evaporated, leaving about 6.5 g of oil which was eluted on a silica gel column with 1% methanol/ethyl acetate via HPLC. The desired fraction was concentrated to 5.0 g of oil which was dissolved in ethyl ether and the solution acidified to pH 1 with ethereal oxalic acid. The resultant precipitate was collected and dried to yield 5.1 g, d @237° C. This material was recrystallized twice from isopropanol/methanol (1:1) to yield 3.5 g of crystals, d @237° C.

| ANALYSIS | | | |
|---|---|---|---|
| Calculated for $C_{26}H_{35}N_3O_6.2C_2H_2O_4$ | 54.13% C | 5.91% H | 6.31% N |
| Found: | 53.85% C | 6.12% H | 6.21% N |

EXAMPLE 17

3-[3-[4-[bis(4-fluorophenyl)methyl]-1-piperazinyl]propyl]-5,6-dimethoxy-1,2-benzisoxazole To 75 ml of dry DMF were added 3-(3-chloropropyl)-5,6-dimethoxy-1,2-benzisoxazole (4.1 g), 1-[bis(4-fluorophenyl)methyl]piperazine (4.3 g), milled $K_2CO_3$ (10 g) and KI (0.01 g).

After six hours of stirring at 90° C., the mixture was poured into 300 ml of water, stirred for five minutes and then extracted with ether/ethyl acetate. The organic layer was washed with water (2X) and dried (saturated NaCl, anhydrous $MgSO_4$).

After filtration, the solvents were evaporated, leaving about 9 g of oil which was eluted on a silica gel column with ethyl acetate via HPLC. The desired fraction was concentrated to 2.8 g of solid, m.p. 163°–8° C. This material was recrystallized twice from isopropyl ether/methanol (3:1) to yield 2.1 g, m.p. 173°–5° C.

| ANALYSIS | | | |
|---|---|---|---|
| Calculated for $C_{29}H_{31}F_2N_3O_3$ | 68.26% C | 6.16% H | 8.28% N |
| Found: | 68.95% C | 6.13% H | 8.33% N |

EXAMPLE 18

3-[3-[4-[(4-chlorophenyl)phenylmethyl]-1-piperazinyl]propyl]-5,6-dimethoxy-1,2-benzisoxazole oxalate To 75 ml of dry DMF were added 3-(3-chloropropyl)-5,6-dimethoxy-1,2-benzisoxazole (5.12 g), 1-[(4-chlorophenyl)phenylmethyl]-piperazine (5.0 g), milled $K_2CO_3$ (10 g) and KI (0.01 g).

After six hours of stirring at 90° C., the mixture was poured into 500 ml of water, stirred for five minutes and then extracted with ethyl acetate. The ethyl acetate layer was washed with water (2X) and dried (saturated NaCl, anhydrous $MgSO_4$).

After filtration, the solvent was evaporated, leaving about 8 g of oil which was eluted on a silica gel column with ethyl acetate via HPLC. The desired fraction was collected, concentrated to 4.5 g of oil, then dissolved in ether, the pH of the solution adjusted to 1 with etheral oxalic acid, and the resultant precipitate collected and dried to yield 4.3 g, d @115° C.

| ANALYSIS | | | |
|---|---|---|---|
| Calculated for $C_{29}H_{32}ClN_3O_2.C_2H_2O_4$: | 62.46% C | 5.75% H | 7.05% N |

| ANALYSIS | | | |
|---|---|---|---|
| Found: | 62.35% C | 5.78% H | 7.13% N |

EXAMPLE 19

3-[3-[4-[4-[bis(4-fluorophenyl)butyl]]-1-piperazinyl]-propyl]-5,6-dimethoxy-1,2-benzisoxazole dioxalate To 75 ml of dry DMF were added 3-(3-chloropropyl)-5,6-dimethoxy-1,2-benzisoxazole (4.1 g), 1-[4,4-bis-(4-fluorophenyl)butyl]piperazine (4.0 g), milled $K_2CO_3$ (10 g) and KI (0.01 g).

After four hours of stirring at 90° C., the mixture was poured into 300 ml of water, stirred for five minutes and then extracted with ethyl acetate (3×100 ml). The organic layer was washed with water (2×100 ml) and saturated NaCl solution (1×100 ml) and then dried over anhydrous $MgSO_4$.

After filtration, the solvent was evaporated, leaving about 9 g of oil which was eluted on a silica gel column with ethyl acetate via HPLC. The desired fractions were combined and concentrated to about 3.8 g of oil which was dissolved in ether and then acidified to pH 1 with etheral-oxalic acid. The resultant precipitate was collected and dried to yield 3.7 g, d @225° C. This material was recrystallized from methanol/water/ether (50:1:5), to yield 3.0 g of crystals, d @228° C.

| ANALYSIS | | | |
|---|---|---|---|
| Calculated for $C_{32}H_{37}F_2N_3 \cdot 2C_2H_2O_4$: | 59.25% C | 5.66% H | 5.76% N |
| Found: | 59.13% C | 5.72% H | 5.69% N |

EXAMPLE 20

3-[3-[4-[3-[6-fluoro-1,2-benzisoxazol-3-yl]propyl]-1-piperazinyl]propyl]-5,6-dimethoxy-1,2-benzisoxazole dioxalate To 100 ml of dry DMF were added 3-(3-chloropropyl)-5,6-dimethoxy-1,2-benzisoxazole (6.4 g), 6-fluoro-3-[3-(1-piperazinyl)propyl]-1,2-benzisoxazole (5.5 g), milled $K_2CO_3$ (10 g) and KI (0.01 g).

After two hours of stirring at 90° C., the mixture was poured into 300 ml of water, stirred for five minutes and then extracted with ether/ethyl acetate (2×150 ml). The organic layer was washed with water (2×100 ml) and saturated NaCl (1×100 ml) and then dried over anhydrous $MgSO_4$.

After filtration, the solvents were evaporated, leaving about 12 g of oil which was eluted on a silica gel column with 5% methanol/DCM. The desired fractions were combined and concentrated to 3 g of solid, which was redissolved in ether, the pH adjusted to 1 with ethereal-oxalic acid and the resultant precipitate collected and dried to yield 2.5 g, d @214° C. This material was recrystallized from methanol/water/ether (50:1:5) to yield 2.1 g of solid, d @221° C.

| ANALYSIS | | | |
|---|---|---|---|
| Calculated for $C_{26}H_{31}FN_4O_4 \cdot 2C_2H_2O_4$: | 54.38% C | 5.32% H | 8.46% N |
| Found: | 54.92% C | 5.37% H | 8.51% N |

EXAMPLE 21

3-[3-[4-[3-[5,6-dimethoxy-1,2-benzisoxazol-3-yl]propyl]-1-piperazinyl]propyl]-5,6-dimethoxy-1,2-benzisoxazole To 80 ml of dry DMF were added 3-(3-chloroproyl)-5,6-dimethoxy-1,2-benzisoxazole (8.9 g), piperazine (1.3 g), milled $K_2CO_3$ (10.0 g) and KI (0.01 g).

After seven hours of stirring at 95° C., the mixture was poured into 500 ml of water, stirred for five minutes and then extracted with ethyl acetate. The organic layer was washed with water (2X) and saturated NaCl solution and then dried over anhydrous $MgSO_4$.

After filtration, the solvent was evaporated, leaving about 10 g of oil which was purified by elution on a silica gel column with 5% methanol/DCM via HPLC. The desired fractions were collected, combined and concentrated to 4.7 g of solid, m.p. 164°–165° C. This material was recrystallized from isopropyl ether/methanol (1:1) to yield 3.0 g of solid, m.p. 166°–7° C.

| ANALYSIS | | | |
|---|---|---|---|
| Calculated for $C_{28}H_{36}N_4O_6$: | 64.10% C | 6.92% H | 10.68% N |
| Found: | 64.54% C | 7.00% H | 10.75% N |

I claim:

1. A compound having the formula

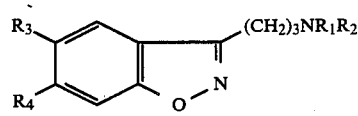

where $R_1$ is hydrogen or loweralkyl; $R_2$ is loweralkyl, arylloweralkyl, diarylloweralkyl or $-CH_2CHOHCH_2OR_5$, $R_5$ being aryl; and $R_3$ and $R_4$ are each independently methoxy or hydroxy, the term aryl in each occurrence signifying a phenyl group having 0, 1, 2 or 3 substituents each of which being independently hydroxy, nitro, loweralkyl, loweralkoxy, halogen or $CF_3$ with the proviso that said aryl may not be trinitrophenyl or triiodophenyl, or a pharmaceutically acceptable acid addition salt thereof.

2. The compound as defined in claim 1, where $R_3$ and $R_4$ are both methoxy.

3. The compound as defined in claim 2, where $R_1$ is hydrogen.

4. The compound as defined in claim 2, where $R_1$ is methyl.

5. The compound as defined in claim 1, where $R_3$ is methoxy and $R_4$ is hydroxy.

6. The compound as defined in claim 5, where $R_1$ is hydrogen.

7. The compound as defined in claim 5, where $R_1$ is methyl.

8. The compound as defined in claim 1, which is N-(phenylmethyl)-5,6-dimethoxy-1,2-benzisoxazole-3-propanamine.

9. The compound as defined in claim 1, which is N-[(2,4-dimethoxy)phenylmethyl]-5,6-dimethoxy-1,2-benzisoxazole-3-propanamine.

10. The compound as defined in claim 1, which is N-methyl-N-(phenylmethyl)-5,6-dimethoxy-1,2-benzisoxazole-3-propanamine.

11. The compound as defined in claim 1, which is N-(2-phenylethyl)-5,6-dimethoxy-1,2-benzisoxazole-3-propanamine.

12. The compound as defined in claim 1, which is N-[2-(4-fluorophenyl)ethyl]-5,6-dimethoxy-1,2-benzisoxazole-3-propanamine.

13. The compound as defined in claim 1, which is N-[2-(4-nitrophenyl)ethyl]-5,6-dimethoxy-1,2-benzisoxazole-3-propanamine.

14. The compound as defined in claim 1, which is N-[2-(3,4-dimethoxyphenyl)ethyl]-5,6-dimethoxy-1,2-benzisoxazole-3-propanamine.

15. The compound as defined in claim 1, which is N-methyl-N-(2-phenylethyl)-5,6-dimethoxy-1,2-benzisoxazole-3-propanamine.

16. The compound as defined in claim 1, which is N-[2-(3,4-dimethoxyphenyl)ethyl]-N-methyl-5,6-dimethoxy-1,2-benzisoxazole-3-propanamine.

17. The compound as defined in claim 1, which is N-[2-(3,4-dimethoxyphenyl)ethyl]-N-methyl-6-hydroxy-5-methoxy-1,2-benzisoxazole-3-propanamine.

18. The compound as defined in claim 1, which is N-[3-(diphenyl)propyl]-N-methyl-5,6-dimethoxy-1,2-benzisoxazole-3-propanamine.

19. The compound as defined in claim 1, which is N-[(2-hydroxy-3-phenoxy)propyl)propyl]-5,6-dimethoxy-1,2-benzisozazole-3-propanamine.

20. A pharmaceutical composition comprising an effective pain alleviating or blood pressure reducing amount of a compound as defined in claim 1 and a suitable carrier therefor.

* * * * *